United States Patent
Randolph

[11] Patent Number: 5,964,404
[45] Date of Patent: Oct. 12, 1999

[54] VACUUM BAG SCENTING SYSTEM

[76] Inventor: Ian Randolph, 2413 East Lakeview Dr., Johnson City, Tenn. 37601

[21] Appl. No.: 09/001,721

[22] Filed: Dec. 31, 1997

[51] Int. Cl.[6] .................................................. A24F 25/00
[52] U.S. Cl. .......................... 239/56; 239/289; 15/246.3; 15/339; 55/380; 55/381; 96/222
[58] Field of Search ................... 239/34, 53–56, 239/289; 15/246.3, 339, DIG. 8; 55/380, 381, DIG. 2; 96/222

[56] References Cited

U.S. PATENT DOCUMENTS

| | | | |
|---|---|---|---|
| 1,828,584 | 10/1931 | Andersen | 15/246.3 X |
| 1,881,086 | 10/1932 | Marshall | 55/380 X |
| 1,954,924 | 4/1934 | Engberg et al. | 15/246.3 X |
| 2,598,129 | 5/1952 | MacFarland | 96/222 |
| 3,685,734 | 8/1972 | Paciorek eta l. | 239/56 |
| 4,277,024 | 7/1981 | Spector | 239/56 X |
| 4,306,892 | 12/1981 | Atalla et al. | 96/222 |
| 4,554,698 | 11/1985 | Rennecker et al. | 15/339 |
| 5,040,264 | 8/1991 | Bryant | 15/339 |
| 5,342,420 | 8/1994 | Bosses | 96/222 |
| 5,415,675 | 5/1995 | Powers et al. | 96/222 |
| 5,461,751 | 10/1995 | Sepke | 15/246.3 |
| 5,503,332 | 4/1996 | Glenn | 239/56 |
| 5,611,486 | 3/1997 | Paul | 239/56 |

*Primary Examiner*—Andres Kashnikow
*Assistant Examiner*—Steven J. Ganey

[57] ABSTRACT

A vacuum bag scenting system is disclosed including a vacuum bag having a pair of faces which are spaced apart upon inflation of the vacuum bag. A closed cellophane bag is disposed in the vacuum bag and coupled to each of the faces of the vacuum bag. A scent pad is disposed in the cellophane bag and is also coupled to a portion of the cellophane bag adjacent one of the faces of the vacuum bag. Inflation of the vacuum bag causes the faces of the vacuum bag to spread apart from each other and in turn tear the cellophane bag apart to expose the scent pad therein to permit releasing of scent from the scent pad into the vacuum bag.

6 Claims, 2 Drawing Sheets

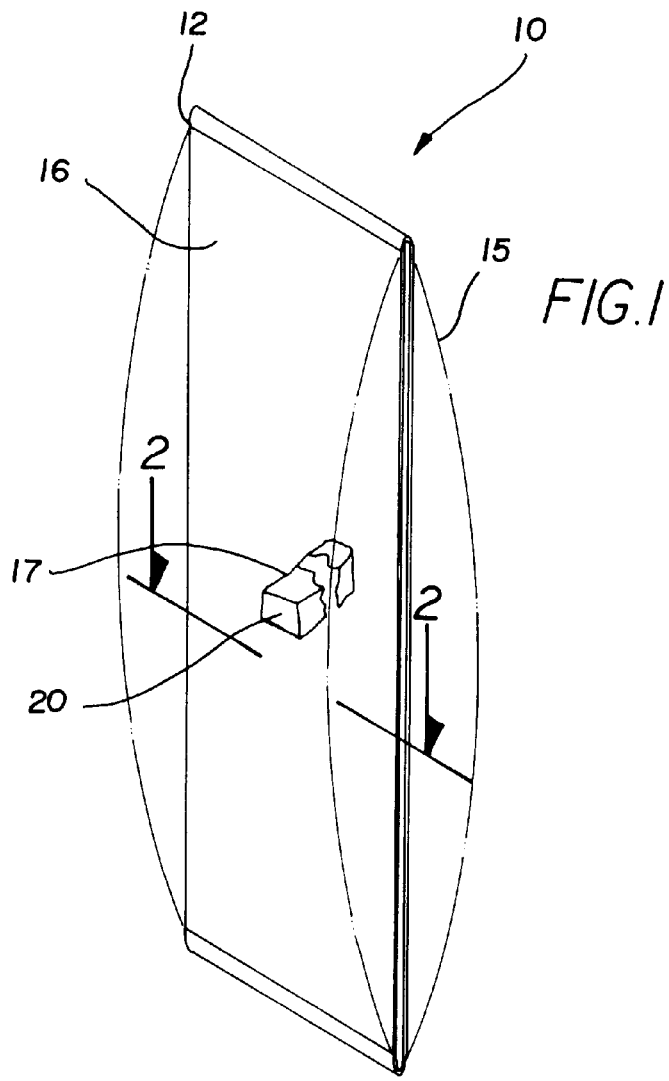
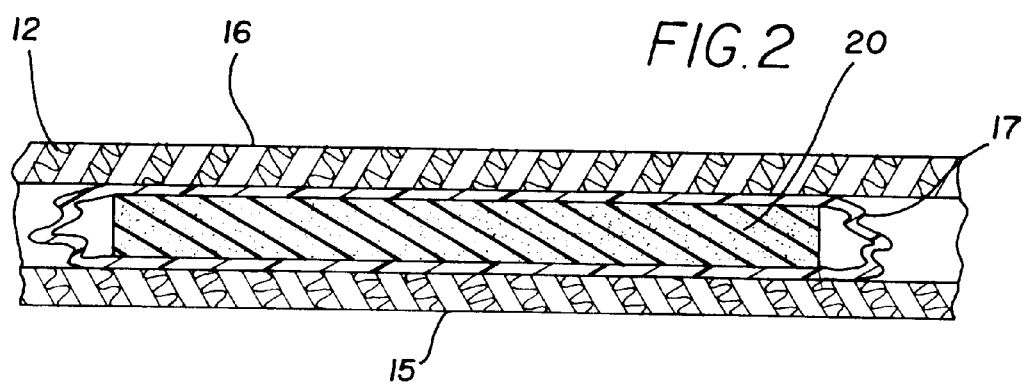

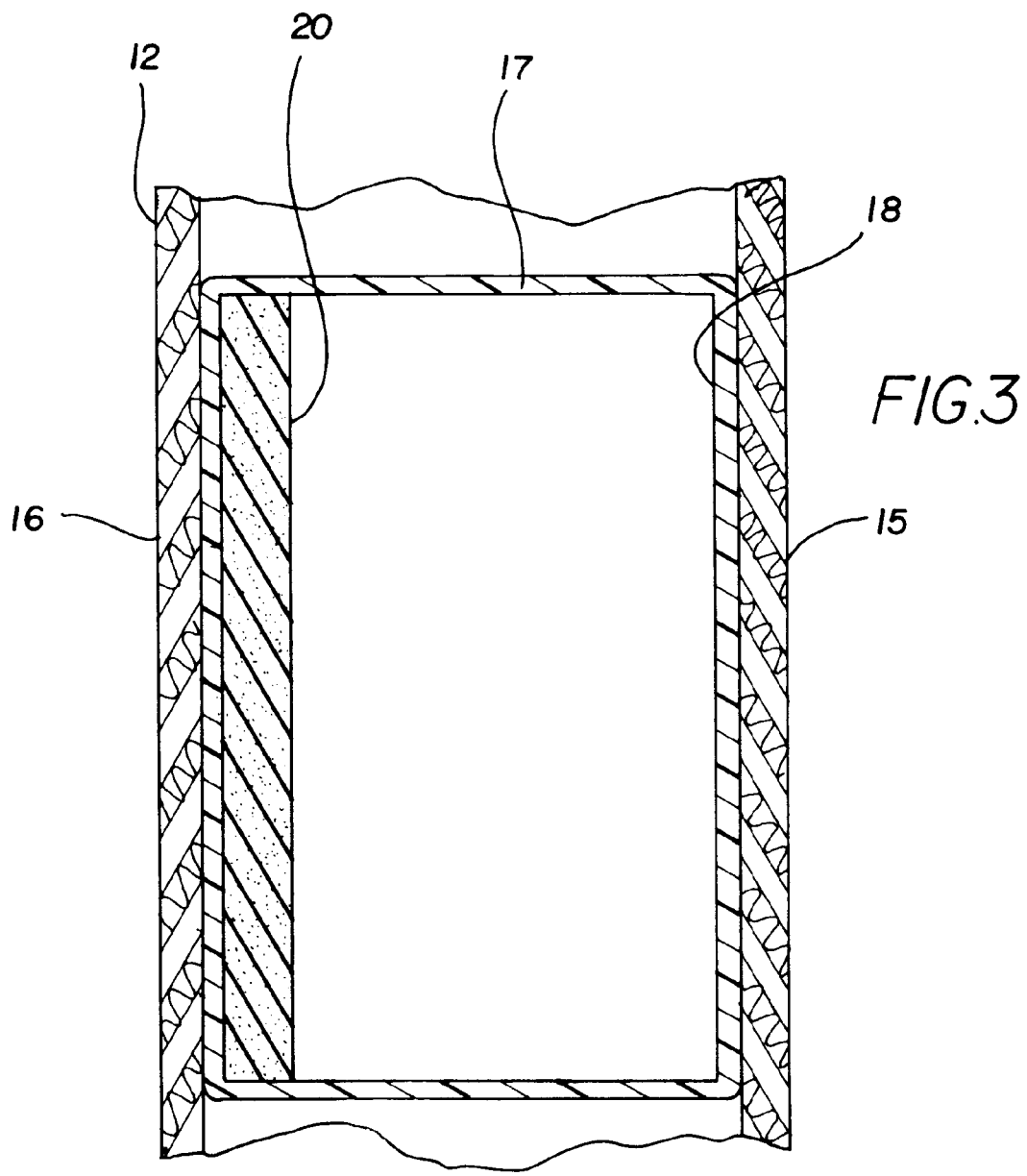

VACUUM BAG SCENTING SYSTEM

BACKGROUND OF THE INVENTION

1. Field of the Invention

The present invention relates to scent pads and more particularly pertains to a new vacuum bag scenting system for providing a pleasant scent when vacuuming.

2. Description of the Prior Art

The use of scent pads is known in the prior art. More specifically, scent pads heretofore devised and utilized are known to consist basically of familiar, expected and obvious structural configurations, notwithstanding the myriad of designs encompassed by the crowded prior art which have been developed for the fulfillment of countless objectives and requirements.

Known prior art scent pads include U.S. Pat. No. 5,087,273; U.S. Pat. No. 4,065,262; U.S. Pat. No. 4,874,129; U.S. Pat. No. 4,306,892; U.S. Pat. No. 5,327,667; and U.S. Pat. No. 5,029,359.

In these respects, the vacuum bag scenting system according to the present invention substantially departs from the conventional concepts and designs of the prior art, and in so doing provides an apparatus primarily developed for the purpose of providing a pleasant scent when vacuuming.

SUMMARY OF THE INVENTION

In view of the foregoing disadvantages inherent in the known types of scent pads now present in the prior art, the present invention provides a new vacuum bag scenting system construction wherein the same can be utilized for providing a pleasant scent when vacuuming.

The general purpose of the present invention, which will be described subsequently in greater detail, is to provide a new vacuum bag scenting system apparatus and method which has many of the advantages of the scent pads mentioned heretofore and many novel features that result in a new vacuum bag scenting system which is not anticipated, rendered obvious, suggested, or even implied by any of the prior art scent pads, either alone or in any combination thereof.

To attain this, the present invention generally comprises a vacuum bag formed of a permeable, flexible material. The bag has a rectangular front and rear face each connected to each other at top and bottom edges thereof. As shown in FIG. 1, a pair of pleated generally elliptical side faces are connected between side edges of the front and rear face of the vacuum bag. Upon the inflation of the bag, a central extent of each of the front and rear faces are distanced a predetermined distance. Next provided is a closed cellophane bag with a cubical configuration. Note FIG. 3. The cellophane bag has a pair of side faces each coupled to an inner surface of the central extent of an opposed one of the front and rear faces. A length of the cube is less than the predetermined distance. As such, when the bag inflates, an intermediate extent of the cellophane bag between the pair of side faces thereof is torn. This exposes an interior space of the cellophane bag. Also included is a scent pad having a planar square configuration with a pair planar side faces and thin periphery. One of the side faces of the scent pad is coupled to the inner surface of the central extent of one of the front and rear faces. By this structure, the cellophane bag is situated between the scent pad and the vacuum bag and the scent pad remains within the cellophane bag only prior to inflation of the vacuum bag.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new vacuum bag scenting system apparatus and method which has many of the advantages of the scent pads mentioned heretofore and many novel features that result in a new vacuum bag scenting system which is not anticipated, rendered obvious, suggested, or even implied by any of the prior art scent pads, either alone or in any combination thereof.

It is another object of the present invention to provide a new vacuum bag scenting system which may be easily and efficiently manufactured and marketed.

It is a further object of the present invention to provide a new vacuum bag scenting system which is of a durable and reliable construction.

An even further object of the present invention is to provide a new vacuum bag scenting system which is susceptible of a low cost of manufacture with regard to both materials and labor, and which accordingly is then susceptible of low prices of sale to the consuming public, thereby making such vacuum bag scenting system economically available to the buying public.

Still yet another object of the present invention is to provide a new vacuum bag scenting system which provides in the apparatuses and methods of the prior art some of the advantages thereof, while simultaneously overcoming some of the disadvantages normally associated therewith.

Still another object of the present invention is to provide a new vacuum bag scenting system for providing a pleasant scent when vacuuming.

Even still another object of the present invention is to provide a new vacuum bag scenting system that includes a vacuum bag and a scent pad situated in communication with the bag.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new vacuum bag scenting system according to the present invention.

FIG. 2 is a cross-sectional view of the pad, vacuum bag and cellophane bag of the present invention taken along line 2—2 shown in FIG. 1.

FIG. 3 is a cross-sectional view of the components of FIG. 2 with the vacuum bag inflated.

DESCRIPTION OF THE PREFERRED EMBODIMENT

With reference now to the drawings, and in particular to FIGS. 1 through 3 thereof, a new vacuum bag scenting system embodying the principles and concepts of the present invention and generally designated by the reference numeral 10 will be described.

The present invention, designated as numeral 10, includes a vacuum bag 12 formed of an air permeable, flexible material. During use, the vacuum bag is adapted to inflate upon the actuation of an associated vacuum cleaner. The bag has a rectangular rear and front face 15 & 16 each connected to each other at top and bottom edges thereof. As shown in FIG. 1, a pair of pleated generally elliptical side faces are connected between side edges of the front and rear face of the vacuum bag. Upon the inflation of the bag, a central extent of each of the front and rear faces are distanced a predetermined distance.

Next provided is a closed cellophane bag 17 with a cubical configuration. Note FIG. 3. It should be understood that the bag may be constructed from any other type of material that may be easily torn. The cellophane bag has a pair of opposed side faces 18 each coupled to an inner surface of the central extent of one of the front and rear faces. Further, the remaining intermediate faces remain loosely situated between the faces of the vacuum bag.

A length of the cube is less than the predetermined distance. As such, when the bag inflates, an intermediate extent of the cellophane bag between the pair of side faces thereof is torn. This exposes an interior space of the cellophane bag. As an option, perforations may be used to facilitate the forgoing tearing.

Also included is a scent pad 20 having a square configuration with a pair planar side faces and thin periphery. Each side face of the scent pad ideally has an area equal to that of the side faces of the cubical cellophane bag. One of the side faces of the scent pad is coupled to the inner surface of the central extent of one of the front and rear faces.

By this structure, the cellophane bag is situated between the scent pad and the vacuum bag and the scent pad remains within the cellophane bag only prior to inflation of the vacuum bag. Once inflated, the vacuum bag tears open the cellophane bag such that scent may be released from the scent pad during the life of the vacuum bag.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A vacuum bag scenting system comprising, in combination:

a vacuum bag formed of a permeable, flexible material and having a rectangular front and rear face each connected to each other at top and bottom edges thereof and a pair of pleated generally elliptical side faces connected between side edges of the front and rear face of the vacuum bag, wherein upon the inflation of the bag, a central extent of each of the front and rear faces is distanced a predetermined distance;

a closed cellophane bag with a cubical configuration and having a pair of side faces each coupled to an inner surface of the central extent of an opposed one of the front and rear faces, wherein a length of the cube is less than the predetermined distance, whereby when the bag inflates, an intermediate extent of the cellophane bag between the pair of side faces thereof is torn thereby exposing an interior space of the cellophane bag; and a scent pad having a planar square configuration with a pair planar side faces and thin periphery, one of the side faces of the scent pad being coupled to the inner surface of the central extent of one of the front and rear faces such that the cellophane bag is situated therebetween and the scent pad remains within the cellophane bag only prior to inflation of the vacuum bag.

2. A vacuum bag scenting system comprising:

a vacuum bag having a pair of faces, the faces of the vacuum bag being spaced apart upon inflation of the vacuum bag;

a closed cellophane bag disposed in the vacuum bag and coupled to each of the faces of the vacuum bag;

a scent pad being disposed in the cellophane bag and being coupled to a portion of the cellophane bag adjacent one of the faces of the vacuum bag, wherein inflation of the vacuum bag tears the cellophane bag to expose the scent pad therein to permit releasing of scent from the scent pad into the vacuum bag.

3. The vacuum bad scenting system of claim 2, wherein the vacuum bag comprises a permeable, flexible material.

4. The vacuum bag scenting system of claim 3, wherein the pair of faces of the vacuum bag each are generally rectangular in shape and are connected to each other at top and bottom edges thereof, wherein the vacuum bag has a pair of pleated generally elliptical sides connected between side edges of the pair of faces of the vacuum bag, wherein upon the inflation of the vacuum bag, a central extent of each of the pair of faces is distanced a predetermined distance.

5. The vacuum bag of claim 4, wherein the cellophane bag has a cubical configuration and a pair of side faces each coupled to an inner surface of the central extent of an opposed one of the pair of faces, wherein a length of the cube is less than the predetermined distance, whereby when the bag inflates, an intermediate extent of the cellophane bag between the pair of side faces thereof is torn thereby exposing an interior space of the cellophane bag.

6. The vacuum bag of claim 5, wherein the scent pad has a planar square configuration with a pair planar side faces and a generally rectangular outer periphery, one of the side faces of the scent pad being coupled to the inner surface of the central extent of one of the front and rear faces such that the cellophane bag is situated therebetween and the scent pad remains within the cellophane bag only prior to inflation of the vacuum bag.

* * * * *